United States Patent [19]
Patterson et al.

[11] Patent Number: 6,156,729
[45] Date of Patent: Dec. 5, 2000

[54] LEUKEMIA INHIBITORY FACTOR FOR USE IN MODULATING INFLAMMATION AND PAIN

[75] Inventors: Paul H. Patterson, Altadena, Calif.; Clifford J. Woolf, Newton, Mass.

[73] Assignee: California Institute of Technology, Pasadena, Calif.

[21] Appl. No.: 09/173,433

[22] Filed: Oct. 15, 1998

Related U.S. Application Data

[60] Provisional application No. 60/062,049, Oct. 15, 1997, abandoned.

[51] Int. Cl.$^7$ .............................. A61K 38/16; A61K 38/00
[52] U.S. Cl. .............................. 514/12; 514/886; 514/887; 424/85.1; 424/85.2; 424/85.4
[58] Field of Search .................................... 514/2, 12, 21, 514/886, 887; 424/85.2, 85.1, 85.4

[56] References Cited

U.S. PATENT DOCUMENTS

| | | | |
|---|---|---|---|
| 5,344,644 | 9/1994 | Igari et al. | 424/85.2 |
| 5,416,071 | 5/1995 | Igari et al. | 514/12 |
| 5,639,275 | 6/1997 | Baetge et al. | 424/422 |

OTHER PUBLICATIONS

Patterson, "Leukemia inhibitory factor, a cytokine at the interface between neurobiology and immunology," *Proc Natl Acad Sci USA*, 91:7833–7835 (Aug. 1994).

Alexander et al., "D–Factor/Leukaemia Inhibitory Factor: Evidence for its Role as a Mediator in Acute and Chronic Inflammatory Disease," *Cytokine*, 6(6):589–586 (Nov. 1994).

Brown et al., "Leukaemeia Inhibitory Factor and Interleukin 6 are Expressed at Very Low Levels in the Normal Adult Mouse and Are Induced by Inflammation," *Cytokine*, 6(3):300–309 (May 19994).

Ulich et al., "Intratracheal injection of LPS and cytokines. V. LPS induces expression of LIF and LIF inhibits acute inflammation," *Amer J. Physiol.*, L443–L 446 (1994).

Heyman et al., "Leukaemia Inhibitory Factor (LIF) Production in Pleural Effusions: Comparison with production of IL–4, IL–8, IL–10 and Macrophage–Colony Stimulating Factor (M–CSF)," *Cytokine*, 5(5):410–416 (May 1996).

Kurek et al., "UP–Regulation of Leukaemia Inhibitory Factor and Interleukin–6 in Transected Sciatic Nerve and Muscle Following Denervation," *Neuromusc Disorders*, 6(2):105–114 (1996).

Banner et al., "Leukemia Inhibitory Factor is Expressed in Astrocytes Following Cortical Brain Injury," *Exper Neurol*, 147:1–9 (1997).

Rao et al., "Leukemia Inhibitory Factor Mediates an Injury Response but Not a Target–Directed Developmental Transmitter Switch in Sympathetic Neurons," *Neuron*, 11:1175–1185 (Dec. 1993).

Corness et al., "Influence of leukemia inhibitory factor on galanin/GMAP and neuropeptide Y expression in mouse primary sensory neurons after axotomy," *Exp Brain Res*, 112:79–88 (1996).

Tham et al., "Leukemia Inhibitory Factor Enhances the Regeneration of Transected Rat Sciatic Nerve and the Function of Reinnervated Muscle," *J Neurosci Res*, 47:208–215 (1997).

Banner et al., "Leukemia Inhibitory Factor Is an Anti–Flammatory and Analgesic Cytokine," *J. Neurosci.*, 18(14):5456–5462 (Jul. 15, 1998).

*Primary Examiner*—F. T. Moezie
*Attorney, Agent, or Firm*—Dolly A. Vance; Richard F. Trecartin; Flehr Hohbach Test Albritton & Herbert LLP

[57] ABSTRACT

A method for inhibiting and/or reducing inflammation and/or pain in an individual is provided. The method comprises administration of leukemia inhibitory factor (LIF) to a cell or an individual in an amount effective to inhibit and/or reduce inflammation and/or pain.

10 Claims, 5 Drawing Sheets

LEUKEMIA INHIBITORY FACTOR FOR USE IN MODULATING INFLAMMATION AND PAIN

This is a continuation of Ser. No. 06/062,049 filed Oct. 15, 1997, now abandoned.

SPONSORSHIP

The U.S. Government has certain rights in this invention pursuant to Grant No. NS 20916 awarded by the National Institute of Health.

FIELD OF THE INVENTION

This invention is related to the use of leukemia inhibitory factor (LIF) and other agonists of the LIF receptor, in the regulation of inflammation and pain.

BACKGROUND

Leukemia inhibitory factor (LIF) belongs to the neuropoietic cytokine family, which also includes ciliary neurotrophic factor (CNTF), oncostatin M (OSM), growth promoting activity, cardiotrophin-1, and interleukin-6 and -11 (IL-6 and IL-11). All of these cytokines are pluripotent, having effects on proliferation and gene expression in a wide variety of cell types in culture. Moreover, all of these cytokines can utilize the same signal transducing receptor subunit, gp130, which exists in a number of different cell types.

LIF has been implicated as having a role in both the neural and immune responses to injury (Patterson PH (1994) *Proc Natl Acad Sci USA* 91:7833–7835). For example, studies have reported that LIF levels are increased in a variety of animal and human inflammatory conditions (Alexander HR, et al, (1994) *Cytokine* 6:589–596; Brown et al, (1994) *Cytokine* 6:300–309; Ulich TR, et al, (1994) *Amer Physiol Soc* 267:442–446; and Heyman D, et al, (1996) *Cytokine* 8:410–416).

Within the nervous system, LIF mRNA levels dramatically increase soon after injury (Patterson PH (1994) *Proc Natl Acad Sci USA* 91:7833–7835; Kurek J B, et al, (1996) *Neuromusc Disorders* 6:105–114; Banner, L R, et al, (1997) *Exper Neurol,* in press), and experiments with LIF null mutant (knockout) mice demonstrate that LIF is required for the changes in neuronal gene expression that are characteristic of the injury response (Rao MS, et al, (1993) *Neuron* 11:1175–1185; Corness J, et al, (1996) *Exp Brain Res* 112:79–88; and Sun Y, Zigmond RE (1996) *Eur J Neurosci* 8:2213–2220). Lack of LIF can also lead to premature neuronal death (Sendtner M, et al, (1996) *Curr Biol* 6:686–694). Moreover, addition of LIF to severed nerves can enhance nerve regeneration and functional recovery (Tham S, et al, (1997) *J Neurosci Res* 47:208–215).

While these studies implicate LIF as having a role in the nervous and immune systems, there is a need to establish the interactions between the nervous and immune systems during the injury response. Accordingly, it is an object herein to determine the role of LIF in response to or in anticipation of injury, trauma or disorders associated with inflammation and/or pain, and to use LIF to modulate inflammation and pain, individually or together.

It is further an object to use biologically active fragments of LIF and other agonists of the LIF receptor to modulate inflammation and/or pain. It is further an object to administer or upregulate LIF or other agonists of the LIF receptor and particularly the signal transducing receptor subunit gp130, in an individual prior to or simultaneous with activities such as sports, hard labor, or undertaking surgery which generally result in inflammation and pain. It is additionally an object to provide a method of using LIF to prevent and/or reduce the inflammation and/or pain associated with Rheumatoid arthritis.

It is also an object herein to provide methods for screening for modulators of LIF and/or LIF activity, particularly those which enhance the anti-inflammatory activity of LIF.

SUMMARY OF THE INVENTION

In accordance with the objectives of the application set forth herein, a method for inhibiting and/or reducing inflammation in an individual is provided. The method comprises administration of leukemia inhibitory factor (LIF) to a cell or an individual in an amount effective to inhibit and/or reduce inflammation.

In one aspect, administration of LIF is prior to an activity or condition which is known to result in inflammation. Alternatively, administration occurs during or preferably, at the onset of the activity or condition.

Administration of LIF in accordance with the present invention is preferably to a site of inflammation or potential inflammation. Administration can be in conjunction with a transdermal formulation, injected or applied topically directly to a site, i.e., an open wound or surgical site.

The methods provided herein also are directed to the administration of LIF to reduce and/or inhibit pain. The method comprises the administration of LIF to an individual in an amount effective to inhibit and/or reduce the pain.

Methods are also provided herein wherein candidate agents are screened for their ability to modulate the activity of LIF. The method comprises administering LIF to a cell or animal model in the presence of the candidate agent and determining the activity of LIF.

BRIEF DESCRIPTION OF THE DRAWINGS

FIG. 1A shows the results on IL-1β, FIG. 1B shows the results on nerve growth factor (NGF), and FIG. 1C shows the results on swelling. Wild type (WT) is shown as +/+ and LIF null mutants are shown as −/−. Swelling is expressed as the change in the dorsal-ventral paw diameter value from pre-inflamed levels in WT (+/+) and LIF (−/−) null mutant mice. The % increase in the mutant mouse was substantially greater (p<0.01 Mann-Whitney U test) than in the WT. N=12 for naive, WT and 6 for all other groups.

FIG. 2A shows results from the LIF knockout mice, and FIG. 2B shows results from wildtype. Hematoxylin and eosin staining of the footpad skin, 48 hours after complete Freund's adjuvant (CFA) injection, reveals more polymorphonuclear neutrophils (arrowhead) in the dermis of (−/−) compared to (+/+). Scale bar denotes 20 mm.

FIG. 3A shows mechanical sensitivity and FIG. 3B shows thermal sensitivity. "**" indicates p<0.001 and "*" indicates p<0.01. N=6 for each data point.

FIG. 4A shows the results of NGF and FIG. 4B shows the results of IL-1β. N=4; *p<0.05 CFA vs. naive; # p<0.05 CFA+100 ng LIF vs. CFA.

DETAILED DESCRIPTION OF THE INVENTION

The role of the neuropoietic cytokine leukemia inhibitory factor (LIF) in the regulation of peripheral inflammation and pain has been investigated. Provided herein are methods for modulating inflammation and inflammatory pain hypersensitivity by up-regulating endogenous LIF or administering LIF, biologically active fragments of LIF or agonists of the LIF receptor.

LIF is known in the art and described in Fukada, PNAS, USA, 82:8495 (1985). The gene for the mouse version of LIF is described in Gearing, et a., EMBO J., 6:3995 (1987). LIF is also described in European Patent Application Publication No. 1285448, published May 10, 1988. LIF is also sometimes referred to as cholinergic neuronal differentiation factor, and is also known as human macrophage differentiation inducing factor (DIF).

In a preferred embodiment, LIF is from vertebrates and more preferably from mammals, including rodents (rats, mice, hamsters, guinea pigs, etc.), primates, farm animals (including sheep, goats, pigs, cows, horses, etc) and in the most preferred embodiment, from humans.

The individual that is administered LIF herein is a vertebrate and more preferably a mammal. The individual can be a rodent as described above, a primate, a farm animal as described above, and in the most preferred embodiment, is a human. Preferably, the individual is in need of or in anticipation of need of an anti-inflammatory or pain-reliever or both.

Administration of LIF can be in combination with one or more further therapeutic agents and includes simultaneous (concurrent) and consecutive administration in any order. The up-regulation or administration of LIF can occur after induction of inflammation or pain, but preferably occurs prior to or simultaneously with induction of inflammation and/or pain. Induction of inflammation and/or pain can be the result of sports- related activities, hard labor, blister-inducing activities or the undertaking of surgery. LIF can also be administered to an individual having Rheumatoid arthritis to reduce swelling and pain associated with arthritis. Generally, inflammatory disorders include any disorder or condition associated with inflammation, i.e., inflammation of the bowel or any other organ, chemically induced inflammation, inflammation due to fire trauma. Each of these conditions, disorders, injuries or inflictions is encompassed by the phrase insult resulting in inflammation or pain.

In one aspect, an agonist of the LIF receptor is administered wherein the agonist reduces and/or prevents inflammation and/or pain. Such agonists include CNTF, OSM, growth promoting activity, cardiotrophin-1, IL-6 and IL-11. The LIF receptor agonist can be administered in combination with other LIF agonists including LIF or a fragment of LIF. A fragment of LIF can be used in the methods provided herein wherein the fragment is biologically active in that it reduces and/or prevents inflammation and/or pain in accordance with the present disclosure. Methods of identification of pain or inflammation reduction or inhibition is further described below.

Inhibition as used herein refers to any delay in the onset of a condition, particularly inflammation or pain. Reduction as used herein refers to a decrease of at least 10%, and more preferably at least a 25% decrease in activity is preferred, with at least about 50% being particularly preferred and about a 95–100% decrease being especially preferred. The reduction is compared to a control concentration of administration of the biologically active composition, wherein the control concentration can be zero.

Inflammation and pain can be determined in a number of ways. Determinations can be made by measuring IL-1beta and nerve growth factor levels (NGF) wherein an increase in either or both of these factors corresponds to a decrease in LIF anti-inflammatory activity.

In an embodiment provided herein, administration of LIF reduces an elevation of IL-1beta by at least 30%, preferably 40%, more preferably 50%, still more preferably 60% and most preferably 70–100%. The reduction is in comparison to a control having a test concentration of LIF, preferably zero.

In another embodiment herein, administration of LIF reduces an elevation of NGF levels by at least 30%, preferably 40%, more preferably 50%, still more preferably 60% and most preferably 70–100%. The reduction is in comparison to a control having a test concentration of LIF, preferably zero.

In a preferred embodiment NGF and IL-1beta levels are inhibited from rising in response to an inflammatory stimuli. In an embodiment provided herein, IL-1beta levels are inhibited by 60% and NGF levels by 50%.

Inflammation can also be determined by direct measurement in size. Swelling can be directly measured by, for example, measuring the diameter of a limb or other body portion.

Another measurement indicating anti-inflammatory activity is the determination of immune cell infiltration, such as the presence of polymorphonuclear neutrophils or macrophages, wherein a decrease in these cell types indicates an anti-inflammatory response and vice versa. Mechanical and thermal hypersensitivity assays can also be used to determine pain sensitivity, increases and decreases.

In a preferred embodiment herein, mechanical (measured by force) and or thermal sensitivity (measured by withdrawal time) can be reduced 2 fold, and preferably at least 3 fold. The onset of pain is preferably delayed by 25% of time and more preferably 50% or more.

In one embodiment herein an individual is administered LIF in anticipation of pain, independent of an inflammatory inducing agent. In this embodiment, thermal sensitivity measured in withdrawal time can be reduced by at least 1 fold, and preferably by at least 2 fold.

In the examples herein, CFA is used as an inflammatory inducing agent. However, as discussed above, a number of conditions or activities result in inflammation.

The LIF, LIF fragments, or LIF receptor agonists of the present invention can be formulated according to known methods to prepare pharmaceutically useful compositions. By way of example, LIF is discussed herein. The pharmaceutical compositions can be formed by combining LIF in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions.

Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG. Slow release polymer formulations are particularly preferred. Transdermal formulations are also preferred.

The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, a vial having a stopper pierceable by a hypodermic injection needle.

The route of administration is in accord with known methods, e.g. injection, intraperitoneal, intracerebral, intramuscular, intraocular, intraarterial or intralesional routes, topical administration, or by sustained release systems. Additionally, LIF or nucleic acids encoding LIF can be administered to cells and then transplanted into the individual. The cells can be autogenic, allogenic, syngenitic or xenogenic, and are preferably autogenic.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. In vivo examples are provided herein. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

Additionally, in an embodiment herein, LIF is modified. Modifications fall into one or more of three classes: substitutional, insertional or deletional. These ordinarily are prepared by site specific mutagenesis of nucleotides in the DNA encoding the LIF protein, using cassette or PCR mutagenesis or other techniques well known in the art, to produce DNA encoding the variant, and thereafter expressing the DNA in recombinant cell culture as outlined above. However, variant LIF protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the LIF protein amino acid sequence. The variants typically exhibit the same qualitative biological activity as the naturally occurring analogue, although variants can also be selected which have modified characteristics as will be more fully outlined below.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. Substitutions, deletions, insertions or any combination thereof may be used to arrive at a final derivative. Generally these changes are done on a few amino acids to minimize the alteration of the molecule. However, larger changes may be tolerated in certain circumstances.

Covalent modifications of LIF polypeptides may be made to use in one or more of the methods provided herein. One type of covalent modification includes reacting targeted amino acid residues of an LIF polypeptide with an organic derivatizing agent that is capable of reacting with selected side chains or the N-or C-terminal residues of an LIF polypeptide. Derivatization with bifunctional agents is useful, for instance, for crosslinking LIF to a water-insoluble support matrix or surface for use in the method for purifying anti-LIF antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the LIF polypeptide comprises altering the native glycosylation pattern of the polypeptide. Altering the native glycosylation pattern is intended for purposes herein to mean deleting one or more carbohydrate moieties found in native sequence LIF polypeptide, and/or adding one or more glycosylation sites that are not present in the native sequence LIF polypeptide.

Addition of glycosylation sites to LIF polypeptides may be accomplished by altering the amino acid sequence thereof. The alteration may be made, for example, by the addition of, or substitution by, one or more serine or threonine residues to the native sequence LIF polypeptide (for O-linked glycosylation sites). The LIF amino acid sequence may optionally be altered through changes at the DNA level, particularly by mutating the DNA encoding the LIF polypeptide at preselected bases such that codons are generated that will translate into the desired amino acids.

Another means of increasing the number of carbohydrate moieties on the LIF polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the LIF polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth Enzymol.*, 138:350 (1987).

Another type of covalent modification of LIF comprises linking the LIF polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Nucleic acids encoding LIF, LIF fragments or LIF receptor agonists may also be used in gene therapy. In gene therapy applications, genes are introduced into cells in order to achieve in vivo synthesis of a therapeutically effective genetic product, for example for replacement of a defective gene. Gene therapy includes both conventional gene therapy where a lasting effect is achieved by a single treatment, and the administration of gene therapeutic agents, which involves the one time or repeated administration of a therapeutically effective DNA or mRNA.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

In a preferred embodiment, the LIF proteins, nucleic acids, modified proteins and cells or animal models (which can be knock out (KO) models, i.e. LIF KO models) containing the same are used in screening assays. Identification of modulators or simulators of LIF activity identified as described herein, permits the design of drug screening assays for compounds that modulate or simulate LIF activity. In particular, modulators that enhance the anti-inflammatory and/or pain reduction activity of LIF can be identified and administered to an individual in need thereof in conjunction with or independently LIF. Modulation is a change of about at least 10–30%, preferably 40–50%, more preferably at least 50–75%, or most preferably, at least 75–100%. As discussed herein, changes in LIF activity can be determined by identification of changes in pain and/or inflammation responses. Such responses can be determined by identification in changes in the presence of NGF, IL-1beta and immune cell infiltrate as well as mechanical and thermal sensitivity and physical swelling.

Screens may be designed to first find candidate agents that can bind to LIF proteins, and then these agents may be used in assays that evaluate the ability of the candidate agent to modulate LIF activity. Thus, as will be appreciated by those in the art, there are a number of different assays which may be run; binding assays and activity assays.

Thus, in a preferred embodiment, the methods comprise combining an LIF protein and a candidate bioactive agent, and determining the binding of the candidate agent to the LIF protein. Preferred embodiments utilize the human LIF protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative LIF proteins may be used, including deletion LIF proteins as outlined above.

Furthermore, included within the definition of LIF proteins are portions of LIF proteins; that is, either the full-length protein may be used, or functional portions thereof. In addition, the assays described herein may utilize either isolated LIF proteins or cells comprising the LIF proteins.

Generally, in a preferred embodiment of the methods herein, the LIF protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In one embodiment, gp130 is used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used.

In a preferred embodiment, the LIF protein is bound to the support, and a candidate bioactive agent is added to the assay. Alternatively, the candidate agent is bound to the support and the LIF protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The term "candidate bioactive agent" or "exogeneous compound" as used herein describes any molecule, e.g., protein, oligopeptide, small organic molecule, polysaccharide, polynucleotide, etc., with the capability of directly or indirectly altering the bioactivity of LIF. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening against LIF. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

The determination of the binding of the candidate bioactive agent to LIF may be done in a number of ways. In a preferred embodiment, the candidate bioactive agent is labelled, and binding determined directly. For example, this may be done by attaching all or a portion of the LIF protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. LIF), such as an antibody, peptide, binding partner, ligand, etc. In one embodiment gp130 is used. Under certain circumstances, there may be competitive binding as between the bioactive agent and the binding moiety, with the binding moiety displacing the bioactive agent.

In a preferred embodiment, the competitor is added first, followed by the candidate bioactive agent. Displacement of the competitor is an indication that the candidate bioactive agent is binding to the LIF protein and thus is capable of binding to, and potentially modulating, the activity of the LIF protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the LIF protein with a higher affinity. Thus, if the candidate bioactive agent is labeled, the presence of the label on the support, coupled with a lack of competitor binding, may indicate that the candidate agent is capable of binding to the LIF protein.

In a preferred embodiment, the methods comprise differential screening to identity bioactive agents that are capable of modulating the activity of the LIF proteins. In this embodiment, the methods comprise combining an LIF protein and a competitor in a first sample. A second sample comprises a candidate bioactive agent, an LIF protein and a competitor. The binding of the competitor is determined for both samples, and a change, or difference in binding between the two samples indicates the presence of an agent capable of binding to the LIF protein and potentially modulating its activity. That is, if the binding of the competitor is different in the second sample relative to the first sample, the agent is capable of binding to the LIF protein.

Alternatively, a preferred embodiment utilizes differential screening to identify drug candidates that bind to the native LIF protein, but cannot bind to modified LIF proteins. The structure of the LIF protein may be modeled, and used in rational drug design to synthesize agents that interact with that site. Drug candidates that affect LIF bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The components provided herein for the assays provided herein may also be combined to form kits. The kits can be based on the use of the protein and/or the nucleic acid encoding the LIF proteins. Assays regarding the use of nucleic acids are further described below.

Screening for agents that modulate the activity of LIF may also be done. In a preferred embodiment, methods for screening for a bioactive agent capable of modulating the activity of LIF comprise the steps of adding a candidate bioactive agent to a sample of LIF, as above, and determining an alteration in the biological activity of LIF. Modulating the activity of LIF can include an increase in activity, a decrease in activity, or a change in the type or kind of activity present. In an embodiment herein, modulating includes inhibition or delay of onset of activity. Thus, in this embodiment, the candidate agent should both bind to LIF (although this may not be necessary), and alter its biological or biochemical activity as defined herein. The methods include both in vitro screening methods, as are generally outlined above, and in vivo screening of cells for alterations in the presence, distribution, activity or amount of LIF.

In a preferred embodiment, the activity of the LIF protein is increased; in another preferred embodiment, the activity of the LIF protein is decreased. Thus, bioactive agents that are antagonists are preferred in some embodiments, and bioactive agents that are agonists may be preferred in other embodiments. Agonists of the LIF receptor and enhancers are preferred. Enhancers act in conjunction with LIF. LIF activity is described above, wherein pain and/or inflammation can be determined in a number of different ways. Changes in activity indicate a modulator.

In a preferred embodiment, the invention provides methods for screening for bioactive agents capable of modulating the activity of an LIF protein. The methods comprise adding a candidate bioactive agent, as defined above, to a cell comprising LIF proteins. Preferred cell types include almost any cell. The cells contain a recombinant nucleic acid that encodes an LIF protein. In a preferred embodiment, a library of candidate agents are tested on a plurality of cells.

In some embodiments, the assays include exposing the cells to an inflammatory agent that will induce inflammation in control cells, i.e. cells of the same type but that do not contain the exogeneous nucleic acid encoding an LIF. Suitable inflammatory agents are known in the art and include but are not limited to CFA or infliction of trauma. Alternatively, the cells may be exposed to conditions that normally result in inflammation, and changes in the normal inflammation progression are determined. Alternatively, the cells can be diseased with an inflammatory disorder or be "knock out" cells as described in the examples. In preferred embodiments, the cells are in an animal model to determine the LIF activity. Alternatively, the cells are in a cell culture taken from an animal model. Thus, the effect of the candidate agent on LIF activity is then evaluated.

The specific examples herein show that levels of LIF mRNA are increased by an inflammatory inducing agent. Also provided are the results of two types of perturbation experiments. LIF levels were either raised acutely through local injection of LIF or they were lowered chronically through the use of mice that lack a functional LIF gene. LIF is shown to suppress inflammation in a LIF knockout mouse, where the response to the inflammatory involves edema, higher levels of inflammatory cytokines and more cellular infiltrate.

Several results from the converse experiment, injecting LIF just prior to the inflammatory inducing agent are also provided herein. For instance, LIF injection at a single time point prior to inflammation has an analgesic action. Moreover, LIF pretreatment diminishes the rise in IL-1β and NGF induced by the inflammatory inducing agent.

Results are also provided wherein an inflammatory agent is not administered after the administration of LIF. Thermal sensitivity was significantly reduced in this embodiment.

The results provided herein show that administration of LIF, biologically active fragments of LIF or other agonists of the LIF receptor can modulate inflammation and pain.

All patent and literature references cited in the present specification are hereby incorporated by reference in their entirety.

The following examples are offered for illustrative purposes only, and are not intended to limit the scope of the present invention in any way.

SPECIFIC EXAMPLES

Methods

Animals. Experiments were performed on adult male Sprague-Dawley rats (200–250 g), as well as wild type (WT) and LIF-deficient mice (Stewart CL, et al, (1992) *Nature* 359:76–79). The mutant mice were maintained by mating within the original colony of the mutant strain, or by back crossing with the C57BI6 parental strain. All of the data reported here on mutant mice comes from the former matings. Null mutants were produced by mating heterozygotes or by mating null males with heterozygote females. Nulls, heterozygotes and WT mice were compared as littermates.

A PCR-based method was used to determine the genotype of the mice. Genomic DNA was isolated from tail biopsies using a spin column DNA isolation kit (Quiagen, Chatsworth, Calif. and 50–100 ng was subjected to PCR amplification (40 cycles: 1 cycle of 5 min. 95° C., 45 sec. 68° C., 45 sec. 72° C.; 38 cycles of 30 sec. 95° C., 45 sec. 68° C., 45 sec. 72° C.; and 1 cycle of 30 sec. 95° C., 45 sec. 68° C., 3 min. 72° C.). Two specific DNA fragments were co-amplified: a 192 bp LIF gene fragment (using a LIF sense primer, 5'-cgcctaacatgacagacttcccat-3', and a LIF antisense primer, 5'-aggccctcatgacgtctatagta-3') and a 541 bp neomycin gene fragment (using a Neo-sense primer, 5'-ccagctcttcagcaatatcacggg-3', and a Neo-antisense primer, 5'-cctgtccggtgccctgaatgaact-3'). The reaction mixture contained 1×PCR buffer (10 mM TrisCI pH=8.3, 50 mM KCI and 0.001% gelatin), 2.5 mM MgCI2, 0.1 mM dNTPs, 0.1 U/µl Taq-polymerase (Promega, Madison, Wis.) and 0.4 pmol/µl primers (each) in a total volume of 15 µl. The amplification products (4. µl) were separated in a 1.5% agarose gel prestained with ethidium bromide, and analyzed on a UV transilluminator. LIF WT mice contained only the LIF product (192 bp), the heterozygotes had both bands (192 and 541 bp), and the LIF-deficient mice had only the larger fragment (541 bp).

Behavior. Thermal and mechanical sensitivity of the rat hindpaw were tested as previously described in detail (Woolf C J, et al, *J Neurosci* 16:2716–2723). Response time (foot withdrawal) on exposure to a hot plate (50° C.) was measured as an index of sensitivity to a noxious thermal stimulus, while the mechanical threshold for eliciting a flexion withdrawal response was measured in grams using calibrated monofilament Von Frey hairs (4.1–72 g). The response of 3 applications of a particular Von Frey hair to the dorsal surface of the foot was tested in each case.

LIF injections. Recombinant human LIF (Preparation 93/562, 1 mg=10000 units; National Institute for Biological Standards and Control, UK) was dissolved in saline at concentrations of a 100 or 1000 ng/ml and injected into the hindpaw under halothane anesthesia (2%) in a volume of a 100 ml.

Inflammation. A unilateral acute inflammatory lesion was produced in rats by an injection into the plantar surface of the hindpaw, under halothane anesthesia (2%), of 100 ml complete Freund's adjuvant (Sigma). In some animals 10 or 100 ng LIF was injected into the dorsal and plantar surfaces of the hindpaw 10 minutes before the CFA injection. In another group of animals LIF was injected 48 hours after CFA administration into the plantar and dorsal surfaces of the hindpaw. For mice, 20 ml of CFA (Sigma) was injected into the left hind hindpaw under ether anesthesia.

LIF, IL-1β and NGF assays. Under deep terminal anesthesia (pentobarbital) samples of hindpaw skin, sciatic nerve and L4 and L5 dorsal root ganglia (DRG) were dissected free, weighed, frozen on dry ice and stored at $-80°$ C. The tissue was sampled for LIF mRNA, IL-1β and NGF using an RNAse protection assay for the first and ELISAs for the second two.

RNAse protection assay. Total RNA was extracted from footpad skin by a standard acid-phenol method. RNA was resuspended in $H_2O$ and stored at $-70°$ C. until use. The structural integrity of the RNA was confirmed with non-denaturing agarose gel electrophoresis. RNAse protection was performed as previously described (Banner, L R, Patterson, P H (1994) *Proc Natl Acad Sci USA* 91:7109–7113), with slight modification of the probe synthesis. Ninety mCi of 32P-GTP (LIF) or -UTP (glyceraldehyde phosphate dehydrogenase; GAPDH) was dried in a 1.5 ml eppendorf tube. The LIF probe was as previously described (Banner, L R, Patterson, P H (1994) *Proc Nati Acad Sci USA* 91:7109–7113) and radioactivity was quantitated by scanning the protected fragments on a Phosphoimager 400S (Molecular Dynamics). The intensity of the radioactive signal emitted by the LIF-protected fragment was compared to the GAPDH-protected fragment as an internal control for the steady-state amount of RNA, and the values expressed in arbitrary units. We have previously shown that GAPDH mRNA levels do not vary in response to injury and thus serves as a good internal control for steady-state RNA levels (Banner, L R, Patterson, P H (1994) *Proc Natl Acad Sci USA* 91:7109–7113).

IL-1β and NGF EllSAs. The tissue was homogenized in phosphate buffered saline (PBS) containing; 0.4 M NaCl, 0.05% Tween 20, 0.5% bovine serum albumin (BSA), 0.1 mM phenylmethylsulfonyl fluoride, 0.1 mM benzethonium chloride, 10 mM EDTA and 20 Kl/ml Aprotinin (Sigma) and the supernatant collected for assay. NGF was measured with a two-site enzyme-linked immunoassay (ELISA) as described before (Safleh-Garabedian B, *Br J Phammacol* 115:1265–1275) using a polyclonal rabbit anti-mouse NGF antiserum raised in our laboratory for coating and a monoclonal antibody (23c4) (Weskamp G, Otten U (1987) *J Neurochem* 48:1779–1786) for detection. An HPLC-purified mouse NGF preparation was used as standard (Promega). IL-1β was measured with a two-site ELISA as previously described (Safieh-Garabedian B, *Br J Phammacol* 115:1265–1275) using immunoaffinity purified sheep polyclonal anti-rat IL-1β antibodies. Recombinant rat IL-1β was used as the standard (provided by Dr. Robert Newton, DuPont-Merck). Results are expressed as ng/hindpaw to deal with the changes in weight of inflamed skin.

Paw diameter. The dorso-ventral thickness of the hindpaw was measured in deeply anesthetized (pentobarbital) animals using a micrometer gauge.

Statistical analysis. Results are presented as mean±SEM. Differences were calculated using Student's or Welch's t test, analysis of variance (ANOVA) followed by Dunnet's Multiple Comparison test, or the Mann-Whitney U-test, where appropriate.

Results

Induced inflammation increases LIF mRNA levels

LIF mRNA levels are altered upon induction of inflammation. Six hours after induction of an acute inflammation of the rat hindpaw by intraplantar injection of CFA, LIF mRNA levels were measured by an RNAse protection assay and expressed as a ratio with GAPDH mRNA. LIF mRNA is elevated in the inflamed skin at 6 hours (4.1±1.8 ipsilateral, 2.8±1.1 contralateral, from naive levels of 1.0; LIF/GAPDH±SEM, n=4), and the trend is a further increase at 48 hour (5.7±2.1 ipsi, 1.4±0.3 contra). The maximal mean relative increase in LIF is 5.7-fold. Smaller, transient increases observed on the contralateral side have been noted for other proteins in this and similar models (Woolf C J, et al, *Br J Pharmacol* 121:417–424). A smaller bilateral change also occurs in the sciatic nerve (2.43±1.10 ipsilateral, 1.86±0.38 contralateral, from naive levels of 1.0; LIF/GAPDH±SEM, n=4, 6 h post CFA). In the ipsilateral L4 and L5 DRG, the LIF/GAPDH value in naive animals is 0.53±0.14 and this increases slightly to 0.88±0.23 at 6 hours post CFA injection.

Inflammation is greater in LIF knockout mice

A stringent test of whether LIF is required for either the development of, or recovery from inflammation is to determine the effects of CFA injection in LIF knockout mice. The general appearance and behavior of WT and LIF knockout mice are similar although the latter are slightly smaller. There is, however, a very significant difference in the response of the two strains to CFA injection. Four hours post-CFA administration, the hindpaws in the mutant mice are very swollen. At 24 and 48 hours the swelling spreads past the ankle and up the calf, and the skin of the foot is under marked tension. In WT mice at these time points, inflammation is limited to the hindpaw and is much less prominent. The difference in dorso-ventral paw diameter at 48 hour post-CFA injection is quantified for the two strains and presented in FIG. 1C. The mean percentage increase in paw diameter is more than twice as great in the LIF knockout mice ($p<0.01$).

Figure 1A:
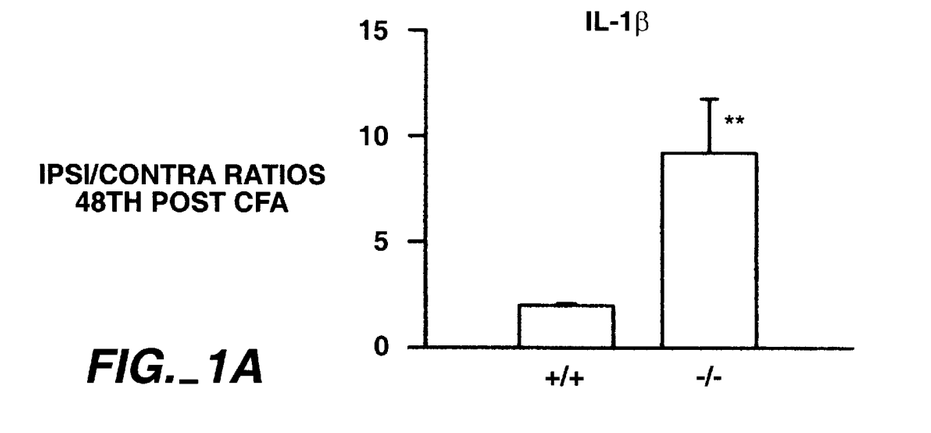
FIGS. 1A, 1B and 1C each show a bar graph indicating the results of LIF knockout mice compared to wild type mice.
Figure 1B:
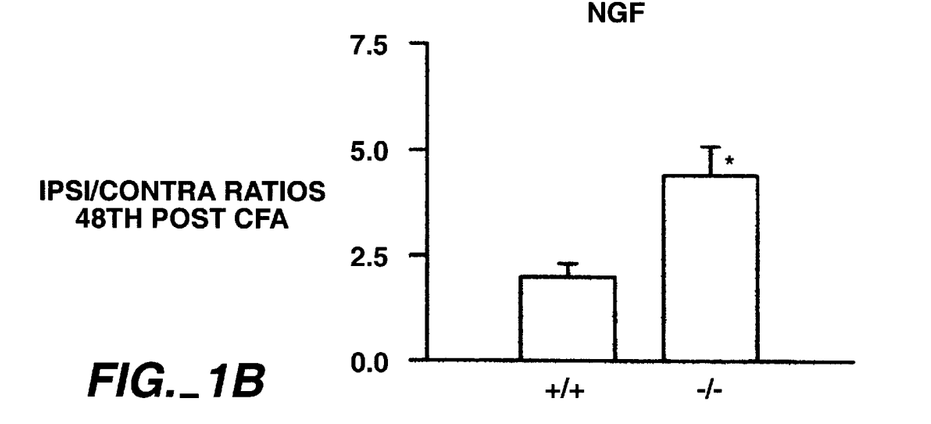
Figure 1C:
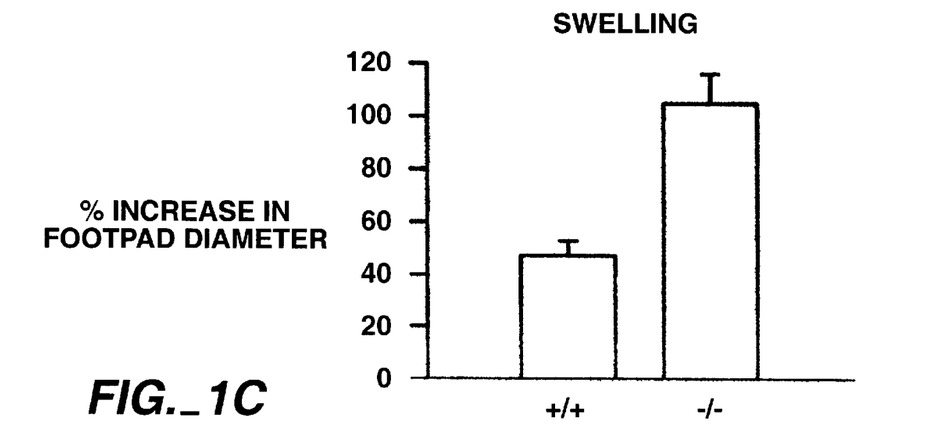

Another assay for inflammation involves quantification of cytokines and growth factors that are elevated under a variety of inflammatory conditions. We find that CFA injection induces a 2-fold elevation in IL-1β, at 24 hour in WT mice (from naive levels of 564±27 pg/hindpaw to 1068±63 pg/hindpaw, n=5). In LIF knockout mice, however, the IL-1β levels at 48 hours post CFA are 1712±364 pg/hindpaw (n=5). When the data are expressed as a ratio of the levels in the inflamed (ipsilateral) and non-inflamed (contralateral) hindpaws at 48 hours, the relative difference is 2-fold in the WT and 9-fold in the mutant mice (FIG. 1A). A similar relative change is detected for NGF levels in the hindpaw, with a significantly greater ratio in mutant versus WT animals (FIG. 1B). At 48 hours the NGF levels in the WT mice are 94.6±10 pg/hindpaw (n=5) while in mutant mice the levels are 186±46 pg/hindpaw (n=5).

Figure 2A:
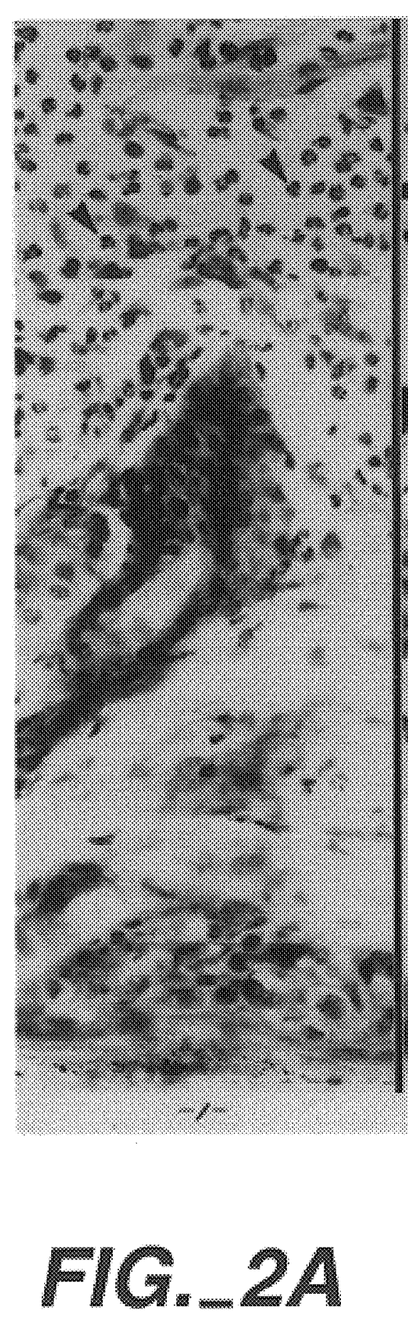
FIGS. 2A and 2B are a photograph showing the results of hematoxylin and eosin staining of footpad skin.
Figure 2B:
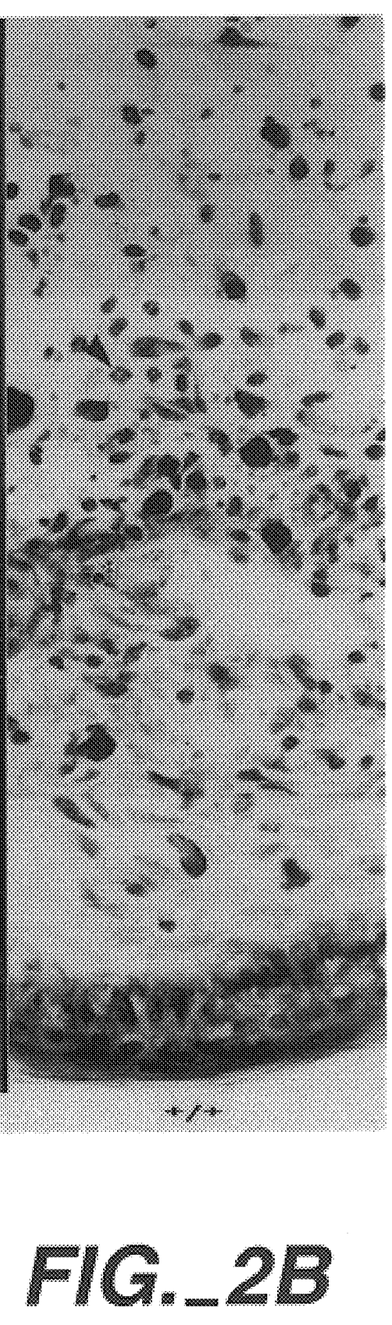

Analysis of the cellular infiltrates in WT and LIF mutant mice reinforce these findings. Staining of the skin 48 hours post-CFA reveals not only a much thicker dermis in the mutants, but many more densely labeled neutrophils (FIG. 2). This difference was quantified by counting cells in 9 sections from 3 animals of each genotype. The LIF mutant mice have 4.75-fold more neutrophils in the inflamed dermis than the WT (+/+, 40.2±7.1; −/−, 190.0±15.1; n=9). When expressed as a density of neutrophils per 100 $\mu$m, the mutants have more than twice as many cells as the WT (+/+, 8.58±0.24; −/−20.83±1.54; $p<0.005$). The mutants also have >2 fold more mast cells than the WT.

Sensitivity to mechanical and thermal stimulation

Figure 3A:
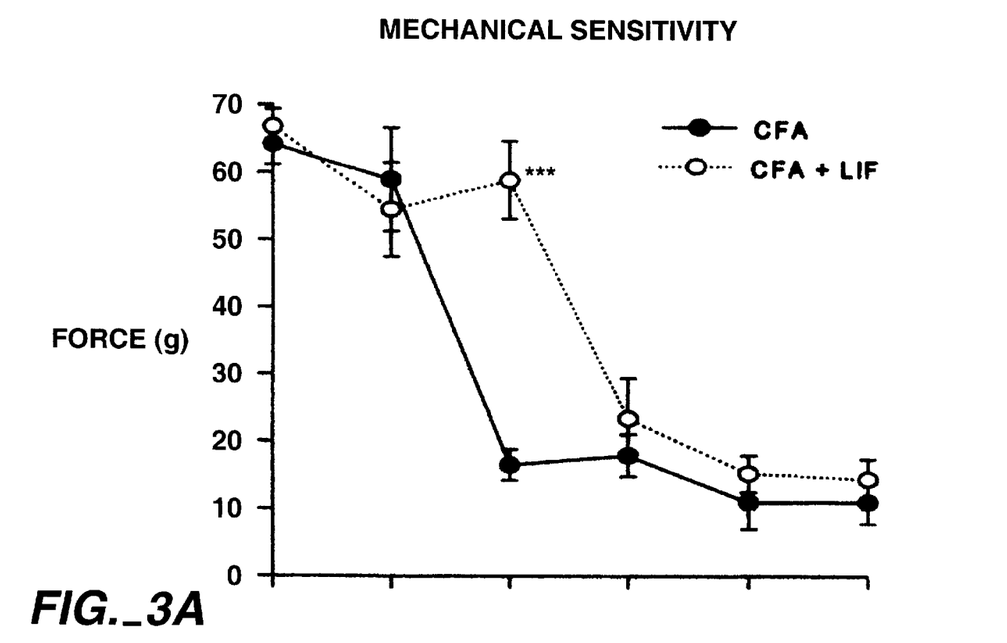
FIGS. 3A and 3B are graphs showing the results of administration of LIF to the paw after inducing inflammation.
Figure 3B:
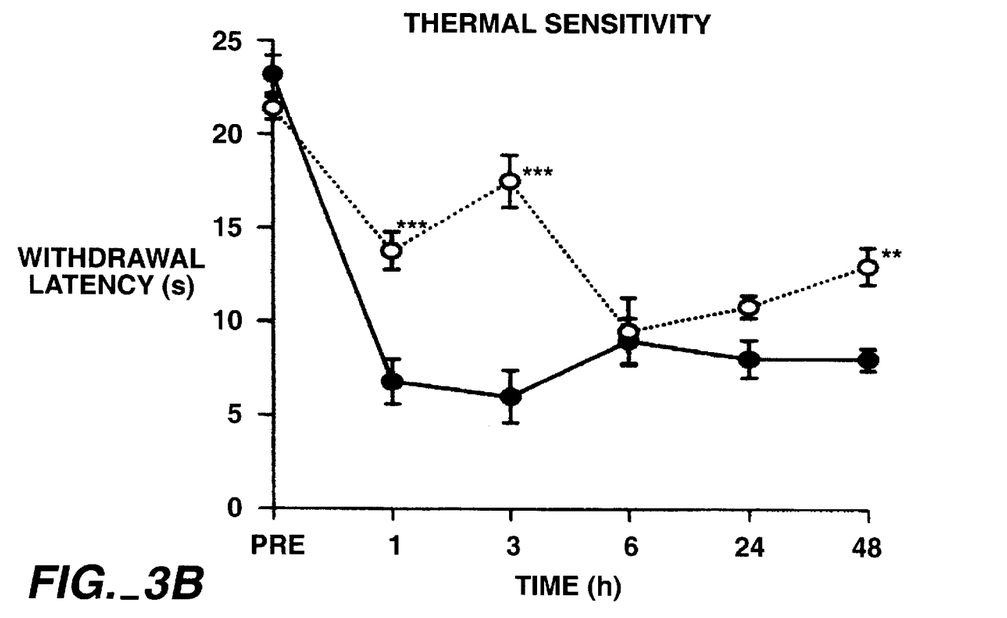
Figure 5:
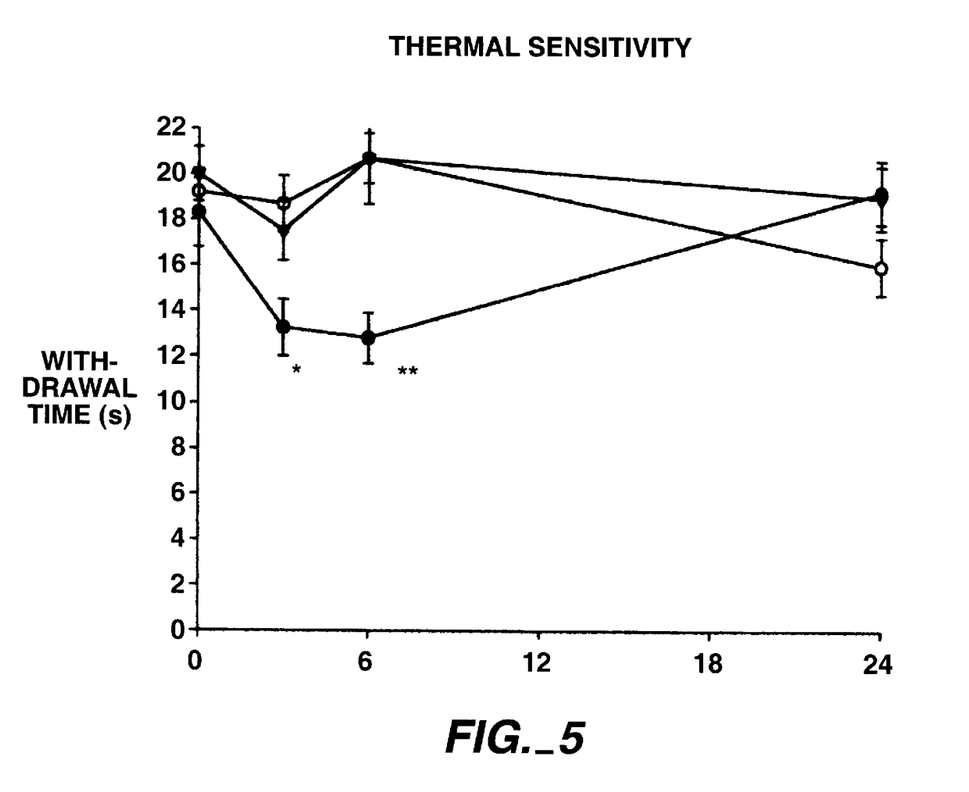
FIG. 5 is a graph showing intraplantar injection of LIF at 50 (diamond), 100 (open circle) and 500 (closed circle) ng into the paws of noninflammed rats. *p<0.05; **p<0.01, N=4 for each data point.

To test whether endogenous LIF acts as an anti-inflammatory agent, we injected LIF into the rat hindpaw 10 minutes before induction of inflammation with CFA. Injection of 100 ng LIF into plantar and dorsal surfaces preceding CFA has a marked effect. Both mechanical and thermal sensitivity in the early phase of inflammation are substantially reduced (FIGS. 3A and 3B). Maximal LIF-induced analgesia in both assays is observed 3 hours post-CFA injection ($p<0.001$). An effect of LIF on thermal sensitivity is also apparent at 48 hour ($p<0.01$). Thus, injection of LIF at a single time point has significant consequences for the subsequent rate and extent of pain associated with inflammation. Also see FIG. 5.

Figure 4A:
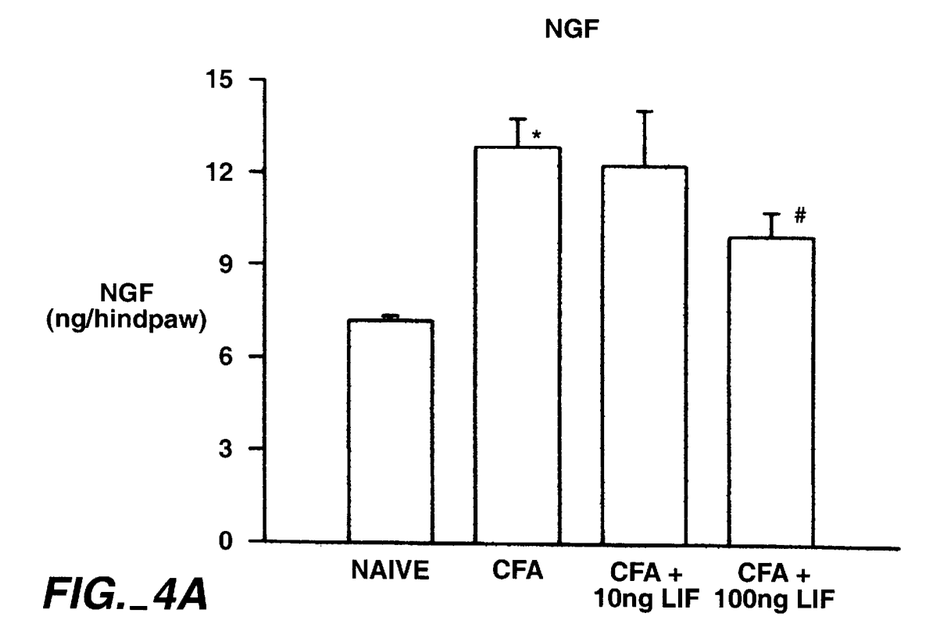
FIGS. 4A and 4B each show a bar graph of LIF knock out mice versus wild type.
Figure 4B:
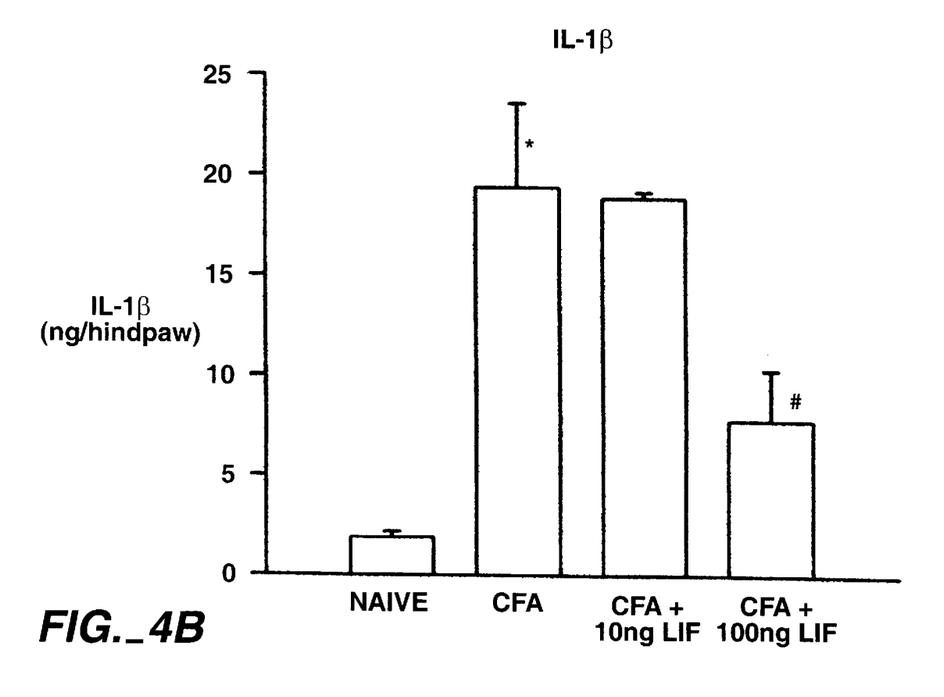

Consistent with its analgesic effects, LIF injection reduces the induction of IL-1β and NGF stimulated by CFA (FIGS. 4A and 4B). Moreover, injection of LIF delays paw swelling and has some affect on reduction in size: 3 hours following CFA treatment the dorsoventral paw diameter increases by 28±6% (n=4) while in the LIF (100 ng)+CFA group this increase is 25±4% (n=4).

It is presumed that LIF exerts its anti-inflammatory, analgesic effects via the Jak-STAT pathway (Inoue M, et al, (1996) *Molec Neurobiol* 12:195–209). Directly or indirectly this leads to the inhibition of the transcription or release of pro-inflammatory cytokines such as IL-1 (FIGS. 1, 4B), or to the release of an anti-inflammatory agent such as IL-1RA (Dinarello Calif. (1996) *Blood* 87:2095–2147). Regarding upstream activators of LIF, TNFα induces LIF in dermal and chondrocyte cultures (Campbell et al, (1993) *Arthritis Rheum* 36:790–794; and Lorenzo J A, et al, *Clin Immunol Immunopathol* 70:260–265), and anti-TNF antibodies attenuate LIF levels in the circulation in primate sepsis (Jansen, P M, et al, (1996) *J Immunol* 156:4401–4407).

Our findings show that LIF is a protective cytokine which is induced early during inflammation and which suppresses expression of cytokines and growth factors that contribute to the inflammatory response and pain. These results indicate that inflammation and pain can be modulated by administration or regulation of LIF and other agonists of the LIF receptor.

The results herein also support that regulation of the gp130 signal transducing subunit utilized by the neuropoietic cytokine family can be used to modulate inflammation and/or pain.

We claim:

1. A method for modulating inflammation in a patient in need thereof or potentially in need thereof, said method comprising administering leukemia inhibitory factor (LIF) to the patient in an amount effective to modulate inflammation.

2. The method of claim 1 where said administering is prior to an insult which results in inflammation.

3. The method of claim 1 where said administering is to the site of inflammation or potential inflammation.

4. The method of claim 1 where said administering of LIF further modulates pain.

5. A method for modulating pain associated with inflammation in a patient in need thereof or potentially in need thereof, said method comprising administering leukemia inhibitory factor (LIF) to an individual in an amount effective to modulate the pain.

6. The me claim 5 where said administering is prior to an insult resulting in pain.

7. The method of claim 5 where said administering is to the site of the pain or potential pain.

8. The method of claim 5 where said administering of LIF also modulates inflammation.

9. The method of claim 1 or 5 wherein said modulating is reducing.

10. The method of claim 1 or 5 wherein LIF is administered to reduce inflammation and pain associated with arthritis.

* * * * *

UNITED STATES PATENT AND TRADEMARK OFFICE
CERTIFICATE OF CORRECTION

PATENT NO.   : 6,156,729
DATED        : December 5, 2000
INVENTOR(S)  : Paul H. Patterson et al.

It is certified that error appears in the above-identified patent and that said Letters Patent is hereby corrected as shown below:

<u>Column 18,</u>
Line 22, change "The me claim" to -- The method of claim --

Signed and Sealed this

Eighteenth Day of March, 2003

JAMES E. ROGAN
*Director of the United States Patent and Trademark Office*